(12) United States Patent
Robinson et al.

(10) Patent No.: US 9,393,282 B1
(45) Date of Patent: Jul. 19, 2016

(54) TOPICAL ANTISEPTIC COMPOSITION

(71) Applicants: Warren Robinson, Elkins Park, PA (US); Frank McAllister, Sr., Elkins Park, PA (US)

(72) Inventors: Warren Robinson, Elkins Park, PA (US); Frank McAllister, Sr., Elkins Park, PA (US)

( * ) Notice: Subject to any disclaimer, the term of this patent is extended or adjusted under 35 U.S.C. 154(b) by 42 days.

(21) Appl. No.: 14/627,144

(22) Filed: Feb. 20, 2015

(51) Int. Cl.
| | |
|---|---|
| *A01N 65/00* | (2009.01) |
| *A61K 36/81* | (2006.01) |
| *A61K 36/73* | (2006.01) |
| *A61K 31/618* | (2006.01) |
| *A61K 31/355* | (2006.01) |
| *A61K 36/63* | (2006.01) |
| *A61K 31/045* | (2006.01) |

(52) U.S. Cl.
CPC ............. *A61K 36/81* (2013.01); *A61K 31/045* (2013.01); *A61K 31/355* (2013.01); *A61K 31/618* (2013.01); *A61K 36/63* (2013.01); *A61K 36/73* (2013.01)

(58) Field of Classification Search
CPC .................................................. A61K 36/00
USPC ................................................... 424/725
See application file for complete search history.

(56) References Cited

U.S. PATENT DOCUMENTS

| | | | |
|---|---|---|---|
| 6,060,062 | A | 5/2000 | Fowler |
| 6,146,639 | A | 11/2000 | Merich |
| 6,589,543 | B1 | 7/2003 | McDaniels |
| 7,368,135 | B1 | 5/2008 | Anderson |
| 8,304,001 | B1 | 11/2012 | Jackson |
| 2009/0123504 | A1 | 5/2009 | Feldkamp et al. |
| 2010/0303935 | A1 | 12/2010 | Squires |

*Primary Examiner* — Michael Meller

(57) ABSTRACT

A topical antiseptic composition includes a mixture consisting of apple vinegar, wintergreen alcohol, cayenne pepper extract, vitamin E, olive oil and menthol.

1 Claim, No Drawings

TOPICAL ANTISEPTIC COMPOSITION

BACKGROUND OF THE DISCLOSURE

Field of the Disclosure

The disclosure relates to antiseptic mixtures and more particularly pertains to a new antiseptic mixture for application to a person's skin.

SUMMARY OF THE DISCLOSURE

An embodiment of the disclosure meets the needs presented above by generally comprising a mixture consisting of apple vinegar, wintergreen alcohol, cayenne pepper extract, vitamin E, olive oil and menthol.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

DESCRIPTION OF THE PREFERRED EMBODIMENT

As best indicated herein, the topical antiseptic composition generally comprises a mixture that may be provided in a liquid form that is typically sprayed on a person's skin. The mixture is used as a topical antiseptic, to relieve pain and to reduce itching of the skin for the areas to which the mixture is applied.

The mixture includes a composition containing apple vinegar, wintergreen alcohol, cayenne pepper extract, vitamin E, olive oil and menthol. More particularly, the wintergreen alcohol is a conventional variation of isopropyl alcohol commonly available and having an isopropyl alcohol content of 50% to 70%. The type of olive oil utilized is not critical to the efficacy of the composition.

More particularly, the composition may comprise by weight:
  18% to 22% apple vinegar
  61% to 65% wintergreen alcohol
  1% to 3% cayenne pepper extract
  3% to 7% vitamin E
  3% to 7% olive oil
  3% to 7% menthol Specifically, the composition may comprise by weight:
  20% apple vinegar
  63% wintergreen alcohol
  2% cayenne pepper extract
  5% vitamin E
  5% olive oil
  5% menthol In use, the composition is sprayed on the skin of the user to reduce pain in the area, reduce dry skin and/or for antiseptic properties.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. An antiseptic, pain relief and itching relief composition for application to the skin of a human in need thereof consisting essentially of:
    between 18% and 22% apple cider vinegar;
    between 61% and 65% isopropyl alcohol;
    between 1% and 3% cayenne pepper extract;
    between 3% and 7% vitamin E;
    between 3% and 7% olive oil; and
    between 3% and 7 menthol.

* * * * *